(12) United States Patent
Appel et al.

(10) Patent No.: US 9,211,261 B2
(45) Date of Patent: Dec. 15, 2015

(54) IMMEDIATE RELEASE DOSAGE FORMS CONTAINING SOLID DRUG DISPERSIONS

(75) Inventors: Leah E. Appel, Bend, OR (US); John E. Byers, Bend, OR (US); Marshall D. Crew, Bend, OR (US); Dwayne T. Friesen, Bend, OR (US); Bruno C. Hancock, North Stonington, CT (US); Stephen J. Schadtle, Milford, CT (US)

(73) Assignee: Bend Research, Inc., Bend, OR (US)

( * ) Notice: Subject to any disclaimer, the term of this patent is extended or adjusted under 35 U.S.C. 154(b) by 1848 days.

(21) Appl. No.: 11/928,426

(22) Filed: Oct. 30, 2007

(65) Prior Publication Data

US 2008/0317851 A1 Dec. 25, 2008

Related U.S. Application Data

(63) Continuation of application No. 10/355,706, filed on Jan. 31, 2003, now abandoned.

(60) Provisional application No. 60/353,840, filed on Feb. 1, 2002.

(51) Int. Cl.
*A61K 9/14* (2006.01)
*A61K 9/20* (2006.01)
*A61K 9/16* (2006.01)

(52) U.S. Cl.
CPC .............. *A61K 9/146* (2013.01); *A61K 9/2081* (2013.01); *A61K 9/1652* (2013.01); *A61K 9/2009* (2013.01); *A61K 9/2027* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 4,950,484 A | 8/1990 | Olthoff et al. | 424/464 |
| 4,999,200 A | 3/1991 | Casillan | 424/480 |
| 5,085,869 A | 2/1992 | Olthoff et al. | 424/499 |
| 5,464,632 A | 11/1995 | Cousin et al. | 424/465 |
| 5,827,541 A | 10/1998 | Yarwood et al. | 424/489 |
| 5,837,292 A | 11/1998 | Dijkgraaf et al. | 424/494 |
| 5,955,107 A | 9/1999 | Augello et al. | 424/465 |
| 5,976,577 A | 11/1999 | Green et al. | 424/490 |
| 5,985,326 A | 11/1999 | Butler | 424/484 |
| 6,004,973 A * | 12/1999 | Guitard et al. | 514/291 |
| 6,059,038 A | 5/2000 | Vick | 166/319 |
| 6,197,786 B1 | 3/2001 | DeNinno et al. | 514/313 |
| 6,224,909 B1 | 5/2001 | Opitz et al. | 424/489 |
| 6,287,596 B1 | 9/2001 | Murakami et al. | 424/464 |
| 6,316,029 B1 | 11/2001 | Jain et al. | 424/484 |
| 6,743,443 B1 * | 6/2004 | Furitsu et al. | 424/465 |
| 6,878,384 B2 | 4/2005 | Cruise et al. | 424/423 |
| 6,964,779 B1 * | 11/2005 | Hayakawa et al. | 424/465 |
| 2001/0053791 A1 * | 12/2001 | Babcock et al. | 514/419 |
| 2002/0006443 A1 | 1/2002 | Curatolo et al. | 424/486 |
| 2002/0012680 A1 | 1/2002 | Patel et al. | 424/400 |
| 2003/0203026 A1 * | 10/2003 | Sherry et al. | 424/469 |
| 2009/0269396 A1 * | 10/2009 | Cipolla et al. | 424/450 |

FOREIGN PATENT DOCUMENTS

| | | | | |
|---|---|---|---|---|
| CA | 2298238 A1 * | 8/2000 | | |
| EP | 0901786 | 3/1999 | | A61K 9/14 |
| EP | 901786 A2 * | 3/1999 | | |
| EP | 1008354 | 6/2000 | | A61K 47/30 |
| EP | 1027887 | 8/2000 | | A61K 9/26 |
| EP | 1027888 | 8/2000 | | A61K 9/26 |
| EP | 1269994 A2 | 1/2003 | | |
| GB | 2351233 | 12/2000 | | A61K 31/445 |
| WO | 02/11710 A2 | 2/2002 | | |

OTHER PUBLICATIONS

Doldan et al. Dicalcium phosphate dihydrate and anhydrous dicalcium phosphate for direct compression: a comparative study, International Journal of Pharmaceutics 124 (1995) 69-74.*
Michel Lemaire, Absorption and Intestinal Metabolism of SDZ-RAD and Rapamycin in Rats, American Society for Pharmacology and Experimental Therapeutics, vol. 27, No. 5, 1999.*
Catellani, P.L., et al., "Tablet Water Uptake and Disintegration Force Measurements", International Journal of Pharmaceutics, vol. 51, pp. 63-66, 1989.
Colombo. P., et al., "Disintegrating Force as a New Formulation Parameter", Journal of Pharmaceutical Sciences, vol. 73, No. 5, pp. 701-705, May 1984.
Massimo, G., et al., "Disintegrating Propensity of Tablets Evaluated by Means of Disintegration Force Kinetics", Pharmaceutical Development and Technology, vol. 5(2), pp. 163-169, 2000.
Sinko, C.M., et al., "The Identification of Percolation and Mechanical Thresholds During the Compaction of Hydroxypropyl methylcellulose: Comparison to Thresholds Determined from Out-of-Die Indentation Experiments", International Journal of Pharmaceutics, vol. 114, pp. 85-93, 1995.
Touitou, E., et al., "Influence of Additives on (hydroxyethyl) Methylcellulose Properties: Relation Between Gelation Temperature Change, Compressed Matrix Integrity and Drug Release Profile," International Journal of Pharmaceutics, vol. 11, pp. 131-148, 1982.
Remington Farrnacia, 19$^{th}$ Ed., Panamericana, Buenos Aires, pp. 423-424, 1999.

* cited by examiner

*Primary Examiner* — Michael G Hartley
*Assistant Examiner* — Nabila Ebrahim
(74) *Attorney, Agent, or Firm* — Klarquist Sparkman, LLP

(57) ABSTRACT

High loading immediate release dosage forms containing at least 30 wt % of a solid drug dispersion, at least 5 wt % of a disintegrant and a porosigen are disclosed that exhibit excellent strength and aqueous solubility.

16 Claims, 2 Drawing Sheets

IMMEDIATE RELEASE DOSAGE FORMS CONTAINING SOLID DRUG DISPERSIONS

CROSS REFERENCE TO RELATED APPLICATIONS

This is a continuation of Ser. No. 10/355,706 filed Jan. 31, 2003, now abandoned the priority of which is claimed, and the priority of Ser. No. 60/353,840 filed Feb. 1, 2002 is also claimed.

BACKGROUND OF THE INVENTION

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability depends on improving the concentration of dissolved drug in solution to improve absorption.

It is well known that the amorphous form of a low-solubility drug that is capable of existing in either the crystalline or amorphous form may temporarily provide a greater aqueous concentration of drug relative to the equilibrium concentration obtained by dissolution of the drug in a use environment. Such amorphous forms may consist of the amorphous drug alone, a dispersion of the drug in a matrix material, or the drug adsorbed onto a substrate. It is believed that such amorphous forms of the drug may dissolve more rapidly than the crystalline form, often dissolving faster than the drug can precipitate from solution. As a result, the amorphous form may temporarily provide a greater-than-equilibrium concentration of drug.

While such amorphous forms may show initially enhanced concentration of the drug in a use environment, nevertheless the improved concentration is often short-lived. Typically, the initially enhanced drug concentration is only temporary and quickly returns to the lower equilibrium concentration.

One approach to increase the bioavailability of low-solubility drugs has involved forming amorphous dispersions of drugs with polymers. Examples of attempts to increase drug concentration by forming a dispersion of the drug with a polymer include Nakamichi et al. U.S. Pat. No. 5,456,923 and Curatolo et al. EP 0901786A2.

When formulating such solid amorphous dispersions into immediate release solid dosage forms for oral administration to a use environment such as the GI tract of an animal such as a human, it is often desirable to maximize the amount of dispersion present in the dosage form. This minimizes the size of the solid dosage form required to achieve the desired dose. Depending on the drug dose, it is often desired that the solid amorphous dispersion comprise at least 30 wt %, preferably at least 40 wt %, and more preferably at least 50 wt % or more of the solid dosage form. Such high drug loadings of dispersion in a solid dosage form minimize the dosage form's size, making it easier for the patient to swallow it and tending to improve patient compliance.

For the ideal immediate release dosage form, the dosage form should have high strength and durability in the solid state, but when ingested, the tablet should rapidly disintegrate and disperse the drug. It is well known how to achieve durability and rapid disintegration for conventional crystalline bulk drug. However, the physical properties of solid amorphous dispersions are very different than conventional crystalline bulk drug, leading to difficulties in imparting such characteristics to dosage forms containing dispersions.

Specifically, in the solid state, solid amorphous dispersions undergo plastic deformation rather than fracture when compressed into a tablet. This can lead to unacceptably low tablet porosity. In addition, when compressed, solid amorphous dispersions adhere better than conventional crystalline bulk drug, due to their plastic flowability and strong surface interactions. The low porosity obtained when solid amorphous dispersions are compressed into a tablet made using conventional tableting formulations leads to slow wicking of water into the tablet, also slowing tablet disintegration. Additionally, when administered to an aqueous environment of use, solid amorphous dispersions can form strong hydrogels, thereby inhibiting rapid tablet disintegration.

The inventors have found that conventional methods of formulating immediate release dosage forms are inappropriate for formulating immediate release dosage forms of solid amorphous dispersions. Specifically, when immediate release tablets comprising a solid amorphous dispersion of a low-solubility drug and a concentration-enhancing polymer are formulated using conventional amounts of tableting excipients used to form conventional immediate release dosage forms, the dosage forms disintegrate too slowly and/or reach maximum concentration in solution too slowly. This problem increases with increasing amount of solid amorphous dispersion in the tablet, particularly when the solid amorphous dispersion content in the tablet reaches approximately 30 to 50% of the total tablet mass. As a result, conventional tablet formulations cannot be used to obtain immediate release dosage forms containing high loadings of such solid amorphous dispersions.

Dosage forms containing solid amorphous dispersions of a specific low solubility drug and concentration-enhancing polymers are disclosed in commonly assigned copending U.S. patent application Ser. No. 09/808,559 filed Mar. 14, 2001. However, no guidelines for selecting excipients for use in forming immediate release dosage forms are provided.

Butler U.S. Pat. No. 5,985,326 discloses the formation of dosage forms containing solid dispersions of two specific poorly soluble drugs in a polymer, the dispersion being formed by coprecipitation of the drug and polymer. Tablets comprising up to 40 wt % of the dispersion were prepared using conventional amounts of conventional tableting excipients. Butler is silent on the disintegration rate or dissolution rate of drug from these dosage forms.

Thus, there is a need in the art for immediate release dosage forms containing large amounts of solid amorphous dispersions that are non-friable, while at the same time exhibiting rapid disintegration and dissolution of the drug.

BRIEF SUMMARY OF THE INVENTION

The present invention overcomes the foregoing prior art drawbacks by providing an immediate release dosage form containing large amounts of a solid amorphous drug dispersion that has high strength and durability, and rapidly disintegrates and/or releases drug when administered to an aqueous environment of use.

The solid amorphous drug dispersion comprises a low-solubility drug and a concentration-enhancing polymer. The polymer is present in the dispersion in an amount sufficient to provide enhancement of the concentration of the drug in a use environment relative to a control composition consisting essentially of an equivalent amount of the drug alone.

In one aspect, the invention provides an immediate release dosage form comprising at least 30 wt % of a solid amorphous drug dispersion formed by spray-drying, at least 5 wt % of a disintegrant and a porosigen that disintegrates in less than 10 minutes following introduction to a disintegration medium or that releases at least 70% of the drug within 15 minutes following introduction to a dissolution medium.

In a second aspect, the invention provides an immediate release dosage form comprising at least 50 wt % of a solid amorphous drug dispersion, at least 5 wt % of a disintegrant and a porosigen where the dosage form has the same disintegration and drug release characteristics as described above.

In a third aspect, the invention also provides a method of treating a disease or condition amenable to treatment with a pharmaceutical agent which is administered in an immediate release dosage form, comprising administering to an animal, including a human, in need of such treatment an immediate release dosage form of the type described above, the dosage form containing an effective amount of the pharmaceutical agent, it being understood that the pharmaceutical agent may be any of the classes of drugs or specific drugs disclosed herein.

The amount of a particular drug which is administered will necessarily be varied according to principles well known in the art, taking into account factors such as the particular drug of interest, the severity of the disease or condition being treated and the size and age of the patient. In general, the drug is to be administered so that an effective dose is received, with the effective dose being determined from safe and efficacious ranges of administration already known for the particular drug of interest.

The dosage forms of the present invention are capable of delivering greater amounts of the solid amorphous dispersion to the desired environment of use in a smaller dosage form than conventional dosage forms and they disintegrate more rapidly and release drug more rapidly to the use environment than conventional dosage forms.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
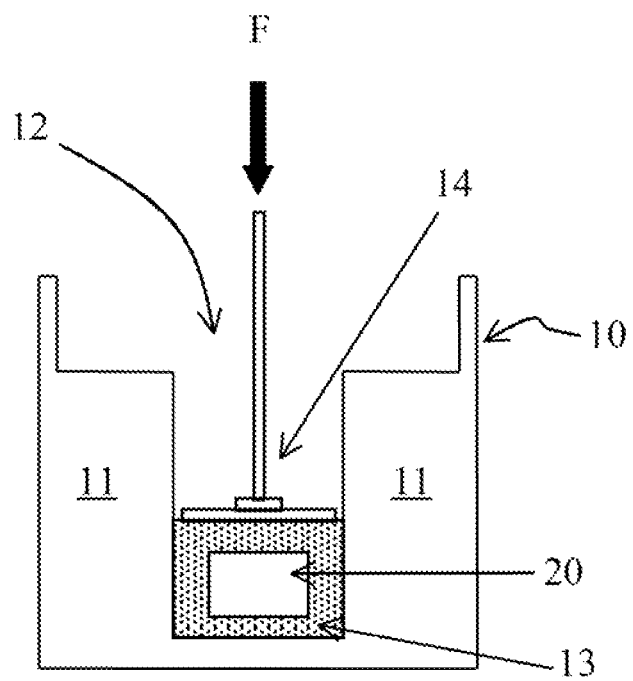
FIG. 1 is a schematic of a dynamic mechanical analyzer (DMA) test apparatus used to evaluate excipients used in the dosage forms of the present invention.

According to the present invention, there is provided a dosage form specifically designed to provide immediate release of low solubility drug in the form of a solid amorphous dispersion to a use environment. By "immediate release" is meant that the dosage form satisfies at least one of the following requirements. First, the dosage form disintegrates in 10 minutes or less following introduction to a disintegration medium, the disintegration time being determined according to the USP XXIV disintegration test procedure, using, for example, a Erweka ZT-71 disintegration tester. Second, the dosage form releases at least 70 wt % of the drug within 15 minutes following introduction to a dissolution medium. A dosage form is considered to be within the scope of this invention if it satisfies either one or both of these requirements.

Reference to a "use environment" can either mean in vivo fluids, such as the GI tract of an animal, including a human, or in vitro fluids, such as a test medium described herein. "Introduction" to a use environment includes either by ingestion or swallowing, where the use environment is in vivo, or being placed in a test medium where the use environment is in vitro. Where release of drug into the stomach is not desired but immediate release of the drug in the duodenum or small intestine is desired, the use environment may also be the duodenum or small intestine. In such cases, "introduction" to a use environment is that point in time when the dosage form leaves the stomach and enters the duodenum.

Suitable low solubility drugs and concentration-enhancing polymers for use in the solid amorphous dispersion, as well as methods for forming the dispersion, and excipients and methods for making the immediate release dosage forms, are discussed in more detail below.

The Drug

The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if the addition of the concentration-enhancing polymer can reduce the size of the dose needed for therapeutic efficacy or increase the rate of drug absorption in cases where a rapid onset of the drug's effectiveness is desired.

The present invention is particularly suitable for preparing immediate release dosage forms containing a solid dispersion that enhances the solubility of a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. The invention finds greater utility as the solubility of the drug decreases. Thus, dosage forms of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and the dose is in mg. Thus, a dose-to-aqueous-solubility ratio may be calculated by dividing the dose (in mg) by the solubility (in mg/mL).

The inventors have recognized a subclass of drugs, referred to herein as "hydrophobic" drugs, that are especially well-suited for use in the dosage forms of the present invention. This subclass of drugs are essentially aqueous insoluble, highly hydrophobic, and are characterized by a set of physical properties. The hydrophobicity of this subclass of drugs not only leads to extremely low aqueous solubility but also tends to make the drugs poorly wetting and slow to dissolve, further reducing their tendency to dissolve and be absorbed from the gastrointestinal tract. Solid amorphous dispersions made using these drugs exhibit dramatic enhancements in aqueous concentration and bioavailability, but often have properties that are difficult to predict based on the nature of the drug. As a result, solid amorphous dispersions made using this subclass of drug often cannot be formulated into an immediate release dosage form using conventional technology known in the art.

The first property of this subclass of essentially aqueous insoluble, hydrophobic drugs is extremely low aqueous solubility. By "extremely low aqueous solubility" is meant that the minimum aqueous solubility at physiologically relevant pH (pH of 1 to 8) is less than about 10 μg/mL and preferably less than about 1 μg/mL.

A second property is a very high dose-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic drugs is a very high dose (in mg) to solubility (in mg/mL) ratio (in mL). By "very high dose-to-solubility ratio" is meant that the dose-to-solubility ratio has a value of at least 500 mL, and preferably at least 1,000 mL.

A third property of this subclass of essentially insoluble, hydrophobic drugs is that they are extremely hydrophobic. By extremely hydrophobic is meant that the Clog P value of the drug has a value of at least 3.0, preferably a value of at least 4.0, and more preferably a value of at least 5.0. Clog P is a widely accepted measure of hydrophobicity, defined as the base 10 logarithm of the ratio of the drug solubility in octanol to the drug solubility in water.

Primarily, as a consequence of some or all of these three properties, drugs of this subclass typically have very low absolute bioavailabilities. Specifically, the absolute bioavailability of drugs in this subclass when dosed orally in their undispersed state is less than about 25% and more often less than about 10%.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein (CETP) inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethyl propyl)-amine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine, and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R⁺S⁺)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; specific examples of CETP inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S]-4-[(3,5-bis-trifluoromethyl-benzyl)- methoxycarbonyl-amino]-2-ethyl-6-trifluoromethyl-3,4-dihydro-2H-quinoline-1-carboxylic acid isopropyl ester.

Concentration-Enhancing Polymers

Concentration-enhancing polymers suitable for use in the solid drug dispersions used in the dosage forms of the invention should be inert, in the sense that they do not chemically react with the drug in an adverse manner. The polymer can be neutral or ionizable, and should have an aqueous solubility of at least 0.1 mg/mL over at least a portion of the pH range of 1-8.

It is preferred that the concentration-enhancing polymer be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution.

A particularly preferred class of amphiphilic polymers are those that are ionizable, the ionizable portions of such polymers constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion-pairing or hydrogen bonds, with ionic or polar groups of the drug. In the case of ionizable polymers, the hydrophilic regions of the polymer would include the ionized functional groups. In addition, the repulsion of the like charges of the ionized groups of ionizable polymers may serve to limit the size of the polymer/drug assemblies to the nanometer or submicron scale. Such drug/concentration-enhancing polymer assemblies in solution may well resemble charged polymeric micellar-like structures. In any case, regardless of the mechanism, the inventors have observed that such amphiphilic polymers, particularly ionizable cellulosic polymers such as those listed below, have been shown to interact with drug so as to maintain a higher concentration of drug in an aqueous use environment.

Another class of polymers suitable for use with the present invention comprises non-ionizable or neutral non-cellulosic polymers. Exemplary polymers include: vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene copolymers.

A preferred class of neutral non-cellulosic polymers are vinyl copolymers of at least one hydrophilic, hydroxyl-containing repeat unit and at least one hydrophobic, alkyl- or aryl-containing repeat unit. Such neutral vinyl copolymers may be termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

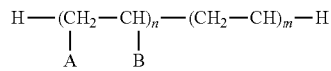

where A and B represent hydrophilic, hydroxyl-containing and hydrophobic substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular weights from about 2,500 to about 1,000,000 daltons.

The hydrophilic, hydroxyl-containing repeat units A may simply be hydroxyl (—OH) or they may be any short chain alkyl (containing 1 to 6 carbons) with one or more hydroxyls attached thereto. The hydroxyl-substituted alkyl may be attached to the vinyl backbone via carbon-carbon or ether linkages. Thus, exemplary A structures include, in addition to hydroxyl itself, hydroxymethyl, hydroxyethyl, hydroxypropyl, hydroxymethoxy, hydroxyethoxy and hydroxypropoxy.

The hydrophobic substituent B may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent B comprises the hydrophilic substituent A to which an alkylate or arylate group is attached via an ester linkage to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer polyvinylbutyrate yields the vinylalcohol/vinylbutyrate copolymer for which A is hydroxyl (—OH) and B is butyrate (–OOC—$CH_2$—$CH_2$—$CH_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as $$H = 100 \times \left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3.

A particularly preferred family of amphiphilic hydroxyl-functional vinyl copolymers are those where A is hydroxyl and B is acetate. Such copolymers are vinylacetate/vinylalcohol copolymers. Some commercial grades are also sometimes referred to simply as polyvinylalcohol. However, the true homopolymer polyvinylalcohol is not amphiphilic and is almost entirely water-insoluble. Preferred vinylacetate/vinylalcohol copolymers are those where H is between about 67% and 99.5%, or n/m has a value between about 2 and 200. The preferred average molecular weight is between about 2500 and about 1,000,000 daltons and more preferably between about 3000 and about 100,000 daltons.

Another class of polymers suitable for use with the present invention comprises ionizable non-cellulosic polymers. Exemplary polymers include: carboxylic acid-functionalized vinyl polymers, such as the carboxylic acid-functionalized polymethacrylates and polyacrylates such as the EUDRAGIT® series manufactured by Rohm Tech Inc., of Maiden, Mass.; amine-functionalized polyacrylates and polymethacrylates; proteins, such as gelatin and albumin; and carboxylic acid-functionalized starches such as starch glycolate.

Non-cellulosic polymers that are amphiphilic are copolymers of a relatively hydrophilic and a relatively hydrophobic monomer. Examples include acrylate and methacrylate copolymers such as the EUDRAGIT® series.

A preferred class of polymers comprises (i) ionizable and (ii) neutral or non-ionizable cellulosic polymers with at least one ester- and/or ether-linked substituent in which the polymer has a degree of substitution of at least 0.05 for each substituent. "Degree of substitution" refers to the average number of the three hydroxyls per saccharide repeat unit on the cellulose chain that have been substituted. For example, if all of the hydroxyls on the cellulose chain have been phthalate-substituted, the phthalate degree of substitution is 3. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Similarly, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.05 to 2.9 as long as the other criteria of the polymer are met. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous-insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers useful in the invention comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at a physiologically relevant pH of from 1 to 8.

Exemplary neutral cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at a physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester-linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at a physiologically relevant pH include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, ethyl carboxymethyl cellulose, cellulose acetate phthalate, carboxymethyl ethyl cellulose, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary ionizable cellulosic polymers that meet the definition of amphiphilic, having hydrophilic and hydrophobic regions include polymers such as cellulose acetate phthalate and cellulose acetate trimeilitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of amphiphilic cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate and carboxymethyl ethyl cellulose.

Of the foregoing cellulosic polymers that are at least partially ionized at a physiologically relevant pH, the inventors have found the following to be most preferred: hydroxypropyl methyl cellulose acetate succinate (HPMCAS), hydroxypropyl methyl cellulose phthalate (HPMCP), cellulose acetate phthalate (CAP), cellulose acetate trimellitate (CAT) and carboxymethyl ethyl cellulose (CMEC). The most preferred is HPMCAS.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "neutralized acidic cellulosic polymers" is meant any cellulosic "acidic polymer" for which a significant fraction of the "acidic moieties" or "acidic substituents" have been "neutralized." By "acidic polymer" is meant any polymer that possesses a significant number of acidic moieties. In general, a significant number of acidic moieties would be greater than or equal to about 0.1 milliequivalents of acidic moieties per gram (meq/g) of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned U.S. Patent Application Ser. No. 60/300,255 filed Jun. 22, 2001, the pertinent disclosure of which is incorporated by reference.

While specific polymers have been discussed as being suitable for use in the dosage forms of the present invention, blends of such polymers may also be suitable. Thus, the term "concentration-enhancing polymer" is intended to include blends of polymers in addition to a single species of polymer.

The amount of concentration-enhancing polymer relative to the amount of drug present in the solid drug dispersions depends on the drug and concentration-enhancing polymer and may vary widely from a drug-to-polymer weight ratio of 0.01 to 5, or from about 1 to about 80 wt % drug. However, in most cases, except when the drug dose is quite low, i.e., 25 mg or less, it is preferred that the drug-to-polymer ratio is greater than 0.05 and less than 2.5 (from about 5 to about 70 wt % drug) and often the enhancement in drug concentration or relative bioavailability is observed at drug-to-polymer ratios of 1 (about 50 wt % drug) or less or for some drugs even 0.2 (about 17 wt % drug) or less. In cases where the drug dose is about 25 mg or less, the drug-to-polymer weight ratio may be significantly less than 0.05. In general, regardless of the dose, enhancements in drug concentration or relative bioavailability increase with decreasing drug-to-polymer weight ratio. However, due to the practical limits of keeping the total mass of a dosage form low, it is often desirable to use a relatively high drug-to-polymer ratio as long as satisfactory results are obtained. The maximum drug:polymer ratio that yields satisfactory results varies from drug to drug and is best determined in the in vitro and/or in vivo dissolution tests described below.

Solid Drug-Containing Dispersion

The drug dispersions used in fabricating the high loading immediate release dosage forms of the present invention comprise solid dispersions of a drug and at least one concentration-enhancing polymer. The concentration-enhancing polymer is present in the dispersions used in the present invention in a sufficient amount so as to improve the concentration of the drug in a use environment relative to a control composition. At a minimum, the dispersions used in the present invention provide concentration enhancement relative to a control consisting of crystalline drug alone. Thus, the concentration-enhancing polymer is present in a sufficient amount so that when the dispersion is administered to a use environment, the dispersion provides improved drug concentration relative to a control consisting of an equivalent amount of crystalline drug, but with no concentration-enhancing polymer present.

Preferably, at least a major portion of the drug in the dispersion is "amorphous," meaning simply that the drug is in a non-crystalline state. As used herein, the term "a major portion" of the drug means that at least 60% of the drug in the dispersion is in the amorphous, as opposed to the crystalline form. Preferably, the drug in the dispersion is "substantially amorphous," meaning that the amount of the drug in crystalline form does not exceed about 25%. More preferably, the drug in the dispersion is "almost completely amorphous," meaning that the amount of drug in the crystalline form does not exceed about 10%. Amounts of crystalline drug may be measured by Powder X-Ray Diffraction (PXRD), Scanning Electron Microscope (SEM) analysis, Differential Scanning Calorimetry (DSC), or any other standard quantitative measurement.

The solid dispersions may contain from about 1 to about 80 wt % drug, depending on the dose of the drug and the effectiveness of the concentration-enhancing polymer. Enhancement of aqueous drug concentrations and relative bioavailability are typically best at low drug levels, typically less than about 25 to about 40 wt %. However, due to the practical limit of the dosage form size, higher drug levels are often preferred and in many cases perform well.

The amorphous drug can exist within the solid amorphous dispersion as a pure phase, as a solid solution of drug homogeneously distributed throughout the polymer or any combination of these states or those states that lie intermediate between them. The amorphous drug is preferably dispersed as homogeneously as possible throughout the polymer so that the dispersion is "substantially homogeneous," meaning that the fraction of drug that is present in relatively pure amorphous domains within the solid dispersion is relatively small, on the order of less than 20%, and preferably less than 10% of the total amount of drug.

While the solid drug dispersion may have some drug-rich domains, it is preferred that the dispersion itself have a single glass transition temperature ($T_g$), which confirms that the dispersion is substantially homogeneous. This is in contrast to a simple physical mixture of pure amorphous drug particles and pure amorphous polymer particles which generally display two distinct $T_g$s, one being that of the drug and one that of the polymer. $T_g$ as used herein is the characteristic temperature where a glassy material, upon gradual heating, undergoes a relatively rapid (i.e., in 10 to 100 seconds) physical change from a glassy state to a rubbery state. The $T_g$ of an amorphous material such as a polymer, drug or dispersion can be measured by several techniques, including by a dynamic mechanical analyzer (DMA), a dilatometer, a dielectric analyzer, and by DSC. The exact values measured by each technique can vary somewhat, but usually fall within 10° to 30° C. of each other. Regardless of the technique used, when an amorphous dispersion exhibits a single $T_g$, this indicates that the dispersion is substantially homogenous. Dispersions that are substantially homogeneous generally are more physically stable and have improved concentration-enhancing properties and, in turn, improved bioavailability, relative to nonhomogeneous dispersions.

The polymer used in the dispersion is a "concentration-enhancing polymer," meaning that it meets at least one, and preferably both, of the following conditions.

The first condition is that the concentration-enhancing polymer increases the maximum drug concentration (MDC) of the drug in the environment of use relative to a control composition consisting of an equivalent amount of the undispersed drug but no polymer. That is, once the composition is introduced into an environment of use, the polymer increases the aqueous concentration of drug relative to the control composition. It is to be understood that the control composition is free from solubilizers or other components that would materially affect the solubility of the drug, and that the drug is in solid form in the control composition. Preferably, the polymer increases the MDC of the drug in aqueous solution by at least 1.25-fold relative to a control composition, more preferably by at least 2-fold, and most preferably by at least 3-fold.

The second condition is that the concentration-enhancing polymer increases the area under the concentration versus time curve (AUC) of the drug in the environment of use relative to a control composition consisting of the undispersed drug but no polymer. The calculation of an AUC is well known in the pharmaceutical arts and is described, for example, in Welling, "Pharmacokinetics Processes and Mathematics," ACS Monograph 185 (1986).) More specifically, the composition comprising the drug and the concentration-enhancing polymer provides an AUC for any 90-minute period of from about 0 to about 270 minutes following introduction to the use environment that is at least 1.25-fold that of the control composition described above. Preferably, the AUC provided by the inventive composition is at least 2-fold, more preferably at least 3-fold that of the control composition.

As previously mentioned, a "use environment" can be either the in vivo environment of the GI tract of an animal, particularly a human, or the in vitro environment of a test solution, such as phosphate buffered saline (PBS) solution or Model Fasted Duodenal (MFD) solution.

The solid drug dispersions used in the inventive dosage forms provide enhanced concentration of the dissolved drug in in vitro dissolution tests. It has been determined that enhanced drug concentration in in vitro dissolution tests in MFD solution or in PBS solution is a good indicator of in vivo performance and bioavailability. An appropriate PBS solution is an aqueous solution comprising 20 mM $Na_2HPO_4$, 47 mM $KH_2PO_4$, 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. In particular, a composition formed by the inventive method can be dissolution-tested by adding it to MFD or PBS solution and agitating to promote dissolution.

An in vitro test to evaluate enhanced drug concentration in aqueous solution can be conducted by (1) adding with agitation a sufficient quantity of control composition, typically the undispersed drug alone, to the in vitro test medium, such as an MFD or a PBS solution, to achieve equilibrium concentration of the drug; (2) adding with agitation a sufficient quantity of test composition (i.e., the drug and polymer) in the same test medium, such that if all the drug dissolved, the theoretical concentration of drug would exceed the equilibrium concentration of the drug by a factor of at least 2, and preferably by a factor of at least 10; and (3) comparing the measured MDC and/or aqueous AUC of the test composition in the test medium with the equilibrium concentration, and/or with the aqueous AUC of the control composition. In conducting such a dissolution test, the amount of test composition or control composition used is an amount such that if all of the drug dissolved, the drug concentration would be at least 2-fold and preferably at least 10-fold that of the equilibrium concentration. Indeed, for some extremely insoluble drugs, in order to identify the MDC achieved it may be necessary to use an amount of test composition such that if all of the drug dissolved, the drug concentration would be 100-fold or even more, that of the equilibrium concentration of the drug.

The concentration of dissolved drug is typically measured as a function of time by sampling the test medium and plotting drug concentration in the test medium vs. time so that the MDC can be ascertained. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid large drug particulates that would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride TITAN® syringe filter sold by Scientific Resources. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It should be recognized that this definition of dissolved drug encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the solid drug dispersions, when dosed orally to a human or other animal, provide an AUC in drug concentration in the blood that is at least about 1.25-fold, preferably at least about 2-fold, and more preferably at least about 3-fold, than that observed when a control composition consisting of an equivalent quantity of undispersed drug is dosed. It is noted that such compositions can also be said to have a relative bioavailability of from about 1.25-fold to about 3-fold that of the control composition.

Relative bioavailability of drugs in the dispersions can be tested in vivo in animals or humans using conventional methods for making such a determination. An in vivo test, such as a crossover study, may be used to determine whether a composition of drug and concentration-enhancing polymer provides an enhanced relative bioavailability compared with a control composition as described above. In an in vivo crossover study a test composition of drug and polymer is dosed to half a group of test subjects and, after an appropriate washout period (e.g., one week) the same subjects are dosed with a control composition that consists of an equivalent quantity of undispersed drug as the test composition (but with no polymer present). The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the drug solubility in vivo.

Preparation of Dispersions

The solid amorphous dispersions of drug and polymer may be made according to any conventional process that results in at least a major portion (at least 60%) of the drug being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray-coating and spray-drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes.

In a melt-congeal or melt-extrusion process, a molten mixture comprising the drug and concentration-enhancing polymer is rapidly cooled to solidify the molten mixture to form a solid amorphous dispersion. By "molten mixture" is meant that the mixture comprising the drug and concentration-enhancing polymer is heated sufficiently that it becomes sufficiently fluid that the drug substantially disperses in one or more of the concentration-enhancing polymers and other excipients. Generally, this requires that the mixture be heated to about 10° C. or more above the melting point of the lowest melting excipient or drug in the composition. The drug may exist in the molten mixture as a pure phase, as a solution of drug homogeneously distributed throughout the molten mixture, or any combination of these states or those states that lie intermediate between them. The molten mixture is preferably substantially homogeneous so that the drug is dispersed as homogeneously as possible throughout the molten mixture. When the temperature of the molten mixture is below the melting point of both the drug and the concentration-enhancing polymer, the molten excipients, concentration-enhancing polymer, and drug are preferably sufficiently soluble in each other that a substantial portion of the drug disperses in the concentration-enhancing polymer or excipients. It is often preferred that the mixture be heated above the lower of the melting points of the concentration-enhancing polymer and the drug.

Generally, the processing temperature may vary from 50° C. up to about 200° C. or higher, depending on the melting point of the drug and polymer, the latter being a function of the polymer grade selected. However, the processing temperature should not be so high that an unacceptable level of degradation of the drug or polymer occurs. In some cases, the molten mixture should be formed under an inert atmosphere to prevent degradation of the drug and/or polymer at the processing temperature. When relatively high temperatures are used, it is often preferable to minimize the time that the mixture is at the elevated temperature to minimize degradation.

The molten mixture may also include an excipient that will reduce the melting temperature of the molten mixture, thereby allowing processing at a lower temperature. When such excipients have low volatility and substantially remain in the mixture upon solidification, they generally can comprise up to 30 wt % of the molten mixture. For example, a plasticizer may be added to the mixture to reduce the melting temperature of the polymer. Examples of plasticizers include water, triethylcitrate, triacetin, and dibutyl sebacate. Volatile agents that dissolve or swell the polymer, such as acetone, water, methanol and ethyl acetate, may also be added to reduce the melting point of the molten mixture. When such volatile excipients are added, at least a portion, up to essentially all of such excipients may evaporate in the process of or following conversion of the molten mixture to a solid mixture. In such cases, the processing may be considered to be a combination of solvent processing and melt-congealing or melt-extrusion. Removal of such volatile excipients from the molten mixture can be accomplished by breaking up or atomizing the molten mixture into small droplets and contacting the droplets with a fluid so that the droplets both cool and lose all or part of the volatile excipient. Examples of other excipients that can be added to the mixture to reduce the processing temperature include low molecular weight polymers or oligomers, such as polyethylene glycol, polyvinylpyrrolidone, and poloxamers; fats and oils, including mono-, di-, and triglycerides; natural and synthetic waxes, such as carnauba wax, beeswax, microcrystalline wax, castor wax, and paraffin wax; long chain alcohols, such as cetyl alcohol and stearyl alcohol; and long chain fatty acids, such as stearic acid. As mentioned above, when the excipient added is volatile, it may be removed from the mixture while still molten or following solidification to form the solid amorphous dispersion.

Virtually any process may be used to form the molten mixture. One method involves melting the concentration-enhancing polymer in a vessel and then adding the drug to the molten polymer. Another method involves melting the drug in a vessel and then adding the concentration-enhancing polymer. In yet another method, a solid blend of the drug and concentration-enhancing polymer may be added to a vessel and the blend heated to form the molten mixture.

Once the molten mixture is formed, it may be mixed to ensure the drug is homogeneously distributed throughout the molten mixture. Such mixing may be done using mechanical means, such as overhead mixers, magnetically driven mixers and stir bars, planetary mixers, and homogenizers. Optionally, when the molten mixture is formed in a vessel, the contents of the vessel can be pumped out of the vessel and through an in-line or static mixer and then returned to the vessel. The amount of shear used to mix the molten mixture should be sufficiently high to ensure uniform distribution of the drug in the molten mixture. The molten mixture can be mixed from a few minutes to several hours, the mixing time depending on the viscosity of the mixture and the solubility of the drug and the presence of optional excipients in the concentration-enhancing polymer.

Yet another method of preparing the molten mixture is to use two vessels, melting the drug in the first vessel and the concentration-enhancing polymer in a second vessel. The two melts are then pumped through an in-line static mixer or extruder to produce the molten mixture that is then rapidly solidified.

Still another method of preparing the molten mixture is by the use of an extruder, such as a single-screw or twin-screw extruder, both well known in the art. In such devices, a solid feed of the composition is fed to the extruder, whereby the combination of heat and shear forces produce a uniformly mixed molten mixture, which can then be rapidly solidified to form the solid amorphous dispersion. The solid feed can be prepared using methods well known in the art for obtaining solid mixtures with high content uniformity. Alternatively, the extruder may be equipped with two feeders, allowing the drug to be fed to the extruder through one feeder and the polymer through the other. Other excipients to reduce the processing temperature as described above may be included in the solid feed, or in the case of liquid excipients, such as water, may be injected into the extruder using methods well known in the art.

The extruder should be designed so that it produces a molten mixture with the drug uniformly distributed throughout the composition. Various zones in the extruder should be heated to appropriate temperatures to obtain the desired extrudate temperature as well as the desired degree of mixing or shear, using procedures well known in the art.

When the drug has a high solubility in the concentration-enhancing polymer, a lower amount of mechanical energy will be required to form the dispersion. In the case where the melting point of the undispersed drug is greater than the melting point of the undispersed concentration-enhancing polymer, the processing temperature may be below the melting temperature of the undispersed drug but greater than the melting point of the polymer, since the drug will dissolve into the molten polymer. When the melting point of the undispersed drug is less than the melting point of the undispersed concentration-enhancing polymer, the processing temperature may be above the melting point of the undispersed drug but below the melting point of the undispersed concentration-enhancing polymer since the molten drug will dissolve in or be absorbed into the polymer.

When the drug has a low solubility in the polymer, a higher amount of mechanical energy may be required to form the dispersion. Here, the processing temperature may need to be above the melting point of the drug and the polymer. As mentioned above, alternatively, a liquid or low-melting point excipient may be added that promotes melting or the mutual solubility of the concentration-enhancing polymer and drug. A high amount of mechanical energy may also be needed to mix the drug and the polymer to form a dispersion. Typically, the lowest processing temperature and an extruder design that imparts the lowest amount of mechanical energy, i.e., shear, that produces a satisfactory dispersion (substantially amorphous and substantially homogeneous) is chosen in order to minimize the exposure of the drug to harsh conditions.

Once the molten mixture of drug and concentration-enhancing polymer is formed, the mixture should be rapidly solidified to form the solid amorphous dispersion. By "rapidly solidified" is meant that the molten mixture is solidified sufficiently fast that substantial phase separation of the drug and polymer does not occur. Typically, this means that the mixture should be solidified in less than about 10 minutes, preferably less than about 5 minutes and more preferably less than about 1 minute. If the mixture is not rapidly solidified, phase separation can occur, resulting in the formation of drug-rich and polymer-rich phases.

Solidification often takes place primarily by cooling the molten mixture to at least about 10° C. and preferably at least about 30° C. below its melting point. As mentioned above, solidification can be additionally promoted by evaporation of all or part of one or more volatile excipients or solvents. To promote rapid cooling and evaporation of volatile excipients, the molten mixture is often formed into a high surface area shape such as a rod or fiber or droplets. For example, the molten mixture can be forced through one or more small holes to form long thin fibers or rods or may be fed to a device, such as an atomizer such as a rotating disk, that breaks the molten mixture up into droplets from 1 µm to 1 cm in diameter. The droplets are then contacted with a relatively cool fluid such as air or nitrogen to promote cooling and evaporation.

A useful tool for evaluating and selecting conditions for forming substantially homogeneous, substantially amorphous dispersions via a melt-congeal or melt-extrusion process is the differential scanning calorimeter (DSC). While the rate at which samples can be heated and cooled in a DSC is limited, it does allow for precise control of the thermal history of a sample. For example, the drug and concentration-enhancing polymer may be dry-blended and then placed into the DSC sample pan. The DSC can then be programmed to heat the sample at the desired rate, hold the sample at the desired temperature for a desired time, and then rapidly cool the sample to ambient or lower temperature. The sample can then be re-analyzed on the DSC to verify that it was transformed into a substantially homogeneous, substantially amorphous dispersion (i.e., the sample has a single Tg). Using this procedure, the temperature and time required to achieve a substantially homogeneous, substantially amorphous dispersion for a given drug and concentration-enhancing polymer can be determined.

Another method for forming solid amorphous dispersions is by "solvent processing," which consists of dissolution of the drug and one or more polymers in a common solvent. "Common" here means that the solvent, which can be a mixture of compounds, will dissolve both the drug and the polymer(s). After both the drug and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Preferably, removal of the solvent results in the formation of a substantially homogeneous, solid amorphous dispersion. In such dispersions, the drug is dispersed as homogeneously as possible throughout the polymer and can be thought of as a solid solution of drug dispersed in the polymer(s), wherein the dispersion is thermodynamically stable, meaning that the concentration of drug in the polymer is at or below its equilibrium value, or it may be considered to be a supersaturated solid solution where the drug concentration in the dispersion polymer(s) is above its equilibrium value.

The solvent may be removed by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in *Perry's Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

Solvents suitable for spray-drying can be any organic compound in which the drug and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a subsequent processing step such as tray-drying. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water, so long as the polymer and drug are sufficiently soluble to make the spray-drying process practicable. Generally, due to the hydrophobic nature of low-solubility drugs, non-aqueous solvents are preferred, meaning that the solvent comprises less than about 10 wt % water.

The solvent-bearing feed, comprising the drug and the concentration-enhancing polymer, can be spray-dried under a wide variety of conditions and yet still yield dispersions with acceptable properties. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) that they do not stick to or coat the spray-drying chamber wall.

Although the maximum droplet size varies widely as a function of the size, shape and flow pattern within the spray-dryer, generally droplets should be less than about 500 µm in diameter when they exit the nozzle. Examples of types of nozzles that may be used to form the dispersions include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. Provisional Application No. 60/353,986 filed Feb. 1, 2002, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the drug or other materials in the dispersion, an inert gas such as nitrogen, nitrogen-enriched air or argon is utilized. The drying gas is typically introduced into the drying chamber at a temperature between about 60° and about 300° C. and preferably between about 80° and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous dispersion instead of separating into drug-rich and polymer-rich phases. In a preferred embodiment, the height and volume of the spray-dryer are adjusted to provide sufficient time for the droplets to dry prior to impinging on an internal surface of the spray-dryer, as described in detail in commonly assigned, copending U.S. Provisional Application No. 60/354,080 filed Feb. 1, 2002, the disclosure of which is incorporated herein by reference. As noted above, to get large enhancements in concentration and bioavailability it is often necessary to obtain as homogeneous a dispersion as possible.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of the drug molecules in the dispersion, thereby improving its stability. Generally, the solvent content of the dispersion as it leaves the spray-drying chamber should be less than 10 wt % and preferably less than 2 wt %. Following formation, the dispersion can be dried to remove residual solvent using a suitable drying processes, such as tray drying, fluid bed drying, microwave drying, belt drying, rotary drying, and other drying processes known in the art.

The dispersion is usually in the form of small particles. The particles may be less than 500 μm in diameter, or less than 100 μm in diameter, less than 50 μm in diameter or less than 25 μm in diameter. When the dispersion is formed by spray-drying, the resulting dispersion is in the form of such small particles. When the dispersion is formed by other methods such by melt-congeal or extrusion processes, the resulting dispersion may be sieved, ground, or otherwise processed to yield a plurality of small particles.

Once the dispersion comprising the drug and concentration-enhancing polymer has been formed, several processing operations can be used to facilitate incorporation of the dispersion into a dosage form. These processing operations include drying, granulation, and milling.

The dispersion may be granulated to increase particle size and improve handling of the dispersion while forming a suitable dosage form. Preferably, the average size of the granules will range from 50 to 1000 μm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof.

If a wet granulation process is used, the granulated composition is often dried prior to further processing. Examples of suitable drying processes to be used in connection with wet granulation are the same as those described above. Where the dispersion is made by a solvent process, the composition can be granulated prior to removal of residual solvent. During the drying process, residual solvent and granulation fluid are concurrently removed from the composition.

Once the composition has been granulated, it may then be milled to achieve the desired particle size. Examples of suitable processes for milling the composition include hammer milling, ball milling, fluid-energy milling, roller milling, cutting milling, and other milling processes known in the art.

Incorporation Into Immediate Release Dosage Forms

Once the dispersion has been made, it is incorporated into an immediate release dosage form. The immediate release dosage form comprises the dispersion, a porosigen, and a disintegrant. The dosage form is in the form of a compressed tablet or other solid dosage form known in the art that utilizes compression forces for formation of the dosage form.

The dosage forms of the present invention contain a high loading of the solid amorphous dispersion. High loadings of dispersion in the dosage form minimize the size of the dosage form, making it easier for the patient to swallow it and improving patient compliance. Depending on the drug dose, the immediate release dosage form comprises at least 30 wt % solid amorphous dispersion. More preferably, the dosage form comprises at least 40 wt %, and most preferably at least 50 wt % of the dispersion. The dosage form may comprise as much as 90 wt % or more of the dispersion and still meet the requirements for the immediate release dosage form.

In one embodiment, the dosage form of the present invention disintegrates in 10 minutes or less following introduction to a disintegration medium. More preferably, the dosage form disintegrates in 5 minutes or less, and most preferably in 2 minutes or less. The disintegration time is determined according to the USP XXIV disintegration test procedure. In this procedure, a dosage form is placed inside a wire basket, the basket being made from a stainless steel wire cloth with 1.8 to 2.2-mm mesh apertures and a wire diameter of 0.60 to 0.655 mm. The wire basket containing the dosage form is raised and lowered in a disintegration medium at a frequency between 29 and 32 cycles per minute. The disintegration medium (typically water) is held at 37° C. An example of an appropriate apparatus for performing such tests is the Erweka ZT-71 disintegration tester. The "disintegration time" is the time required to render any residue of the dosage form remaining on the wire basket a soft mass having no palpably firm core, excluding fragments of insoluble coating.

In another embodiment, the dosage form of the present invention releases at least 70 wt %, more preferably at least 80 wt % and most preferably at least 90 wt % of the low solubility drug within 15 minutes following introduction to a dissolution medium.

An in vitro test may be used to determine whether a dosage form provides a release profile within the scope of the present invention. In vitro tests are well known in the art. One example is a so-called "direct" test, where the dosage form is placed into a stirred USP type 2 dissoette flask containing 900 mL of a dissolution medium maintained at 37° C., such as a buffer solution simulating a gastric environment (10 mM HCl, 100 mM NaCl, pH 2.0, 261 mOsm/kg) or the PBS or MFD solutions previously described. One skilled in the art will understand that in such tests the dissolution medium should act as a sink for the drug in the dosage form. By "sink" is meant that the composition and volume of the dissolution medium is sufficient such that substantially all of the drug in the dosage form will dissolve into the dissolution medium within about 4 hours or less. In some cases a surfactant, such as sodium lauryl sulfate or other excipients may be added to the dissolution medium to ensure the dissolution medium acts as a sink for the drug. The dosage form is placed in a wire support to keep the dosage form off of the bottom of the flask, so that all of its surfaces are exposed to the dissolution medium, and the medium is stirred using paddles that rotate at a rate of 50 rpm. Samples of the dissolution medium are taken at periodic intervals using a VanKel VK8000 autosampling dissoette with automatic receptor solution replacement. The concentration of dissolved drug in the dissolution medium is then determined by High Performance Liquid Chromatography (HPLC), by comparing UV absorbance of samples to the absorbance of drug standards. The mass of dissolved drug in the dissolution medium is then calculated from the concentration of drug in the medium and the volume of the medium, which value is used to calculate the actual amount of drug released from the dosage form, taking into consideration the mass of drug originally present in the dosage form.

Although an in vivo test may be used to determine whether a dosage form provides a drug release profile within the scope of the present invention, and even though the ultimate use environment is often the human GI tract, due to the inherent difficulties and complexity of in vivo tests, it is preferred that in vitro tests be used to evaluate dosage forms.

In addition to the dispersion, the dosage form of the present invention also comprises a disintegrant. Examples of disintegrants include sodium starch glycolate, sodium carboxymethyl cellulose, calcium carboxymethyl cellulose, croscarmellose sodium, crospovidone, polyvinylpolypyrrolidone, methyl cellulose, microcrystalline cellulose, powdered cellulose, lower alkyl-substituted hydroxypropyl cellulose, polacrilin potassium, starch, pregelatinized starch, sodium alginate, and mixtures thereof. Of these, crospovidone, croscarmellose sodium, lower alkyl-substituted hydroxypropyl cellulose, methyl cellulose, polacrilin potassium and mixtures thereof are preferred, with crospovidone, croscarmellose sodium and mixtures thereof being most preferred. In one embodiment, the disintegrant comprises 50 wt % crospovidone and 50 wt % croscarmellose sodium. The amount of disintegrant included in the dosage form will depend on several factors, including the properties of the dispersion, the properties of the porosigen (discussed below), and the properties of the disintegrant selected. Generally, the disintegrant will comprise from 1 wt % to 25 wt %, preferably from 5 wt % to 20 wt % of the dosage form.

When introduced to an aqueous environment of use, the tablet rapidly takes up water, leading to swelling of the disintegrant and rapid disintegration of the tablet before the dispersion polymer can form a hydrogel. The disintegrant should be chosen such that it (1) swells rapidly when introduced into the use environment and (2) has a low tendency to form or promote formation of a hydrogel. The inventors have found that the rate of swelling of the disintegrant is directly correlated to tablet disintegration times—that is, tablets containing disintegrants that cause more rapid swelling have faster disintegration times at comparable disintegrant levels.

The amount of work, W, or swelling energy, due to swelling can be measured using a dynamic mechanical analyzer (DMA), as exemplified in FIG. 1. An appropriate DMA is the Model 7e from Perkin Elmer of Norwalk, Conn. A compact of disintegrant 20 weighing about 50 mg is placed into sample holder 11 and a multiplicity of 90-150 μm diameter glass beads 13 are used to surround and support the compact in liquid reservoir 12, thereby facilitating the compact's rapid and uniform exposure to the liquid. The reservoir, beads, and sample are heated and held at 37° C. for the duration of the experiment. A constant force of about 5 N is applied to the sample by probe 14. Water is then added to the liquid reservoir 12 and the change in displacement of probe 14 is measured as a function of time. From this change in displacement of probe 14, the change in volume of the compact is calculated. The swelling energy attributable to swelling of the disintegrant in the compact may be calculated from the following equation $$W = P \cdot \Delta V,$$

where W is the work or swelling energy of the disintegrant, P is the pressure applied by the probe, and $\Delta V$ is the volume change of the sample. To compare disintegrants, the swelling energy per mass of disintegrant is used. Preferably, the disintegrant generates a swelling energy of at least 0.05 J/g within about 10 minutes, more preferably within about 7 minutes, and most preferably within about 5 minutes following addition of water to the liquid reservoir.

The dosage form of the present invention also includes a porosigen. A "porosigen" is a material that, when present in the formulation containing the solid amorphous dispersion, leads to a high porosity and high strength following compression of the blend into a tablet. In addition, preferred porosigens are soluble in an acidic environment with aqueous solubilities typically greater than 1 mg/mL at a pH less than about 5. Generally, the predominant deformation mechanism for porosigens under compression is brittle fracture rather than plastic flow. Examples of porosigens include acacia, calcium carbonate, calcium sulfate, calcium sulfate dihydrate, compressible sugar, dibasic calcium phosphate (anhydrous and dihydrate), tribasic calcium phosphate, monobasic sodium phosphate, dibasic sodium phosphate, lactose, magnesium oxide, magnesium carbonate, silicon dioxide, magnesium aluminum silicate, maltodextrin, mannitol, methyl cellulose, microcrystalline cellulose, sorbitol, sucrose, xylitol and mixtures thereof. Of these, microcrystalline cellulose, both forms of dibasic calcium phosphate (anhydrous and dihydrate), and mixtures thereof are preferred. As with the disintegrant selection, the amount of porosigen included in the dosage form will depend on the properties of the dispersion, the disintegrant and the porosigen selected. Generally, the porosigen will comprise from 5 to 70 wt %, and preferably from 10 to 50 wt % of the dosage form.

Tablets are generally formed by blending the dispersion, disintegrant, and porosigen, with optional excipients, and then compressing the powder to form tablets using any of a wide variety of presses used in the fabrication of pharmaceutical dosage forms. Often it is desirable to granulate the compositions themselves, with or without the addition of excipients prior to compression. For example, the dispersion, disintegrant, and porosigen may be granulated by mechanical means by, for example, roller compaction or "slugging," followed by milling to form granules. The granules typically have improved flow, handling, blending, and compression properties relative to the ungranulated materials. Wet granulation techniques may also be employed, provided the solvents and process selected do not alter the properties of the solid amorphous dispersion. Improved wetting, disintegrating, dispersing and dissolution properties may be obtained by the inclusion of other excipients, as described below.

After the tablet is formed by compression, it is desired that the dispersion, disintegrant, and porosigen result in a tablet that has a "strength" of at least 5 Kiloponds (Kp)/cm$^2$, preferably at least 10 Kp/cm$^2$. Here, "strength" is the fracture force, also known as the tablet "hardness," required to fracture a tablet formed from the materials, divided by the maximum cross-sectional area of the tablet normal to that force. The fracture force may be measured using a Schleuniger Tablet Hardness Tester, model 6D. To achieve the desired strength, the mixture of dispersion, disintegrant, and porosigen should be compressed with sufficient force while forming the tablets. The compression force required to achieve this strength will depend on the size of the tablet, but generally will be greater than about 5 kP/cm$^2$. Friability is a well-known measure of a tablet's resistance to surface abrasion that measures weight loss in percentage after subjecting the tablets to a standardized agitation procedure. Friability values of from 0.8 to 1.0% are regarded as constituting the upper limit of acceptability. Tablets having a strength of greater than 5 kP/cm$^2$ generally are very robust, having a friability of less than 0.5%, preferably less than 0.1%.

However, if too high a compression force is used, the porosity of the tablet decreases, slowing the rate of water wicking into the tablet, resulting in increased disintegration times and/or dissolution rates. Tablet porosity ∈ is defined as follows:

$$\varepsilon = \frac{\text{Tablet void volume}}{\text{Tablet actual volume}}$$
$$= \frac{V_{void}}{V_{tablet}}$$
$$= 1 - \frac{\text{Volume of tablet ingredients}}{V_{tablet}}$$
$$= 1 - \frac{V_{ingredients}}{V_{tablet}}.$$

Tablet actual volume is determined by the size and shape of the tablet. Volume of the tablet ingredients is determined by the following equation:

$$V_{ingredients} = \sum_i \frac{m_i}{\rho_i},$$

where $m_i$ is the mass of ingredient i used in the tablet, and $\rho_i$ is the intrinsic or true density of ingredient i, i.e., the density of the material without any pores or porosity. The intrinsic density of most excipients is provided by the manufacturer.

To ensure the tablet has sufficient porosity to allow adequate wicking of water into the tablet to cause rapid tablet disintegration and/or rapid release of drug, tablet porosity should be at least 0.15, more preferably at least 0.20, and most preferably at least 0.25. Accordingly, the disintegrant and porosigen should be selected so that the immediate release dosage form has high strength as well as the high porosity required to achieve rapid disintegration and/or release of drug when the dosage form is introduced to a use environment.

In a preferred embodiment, the immediate release dosage form comprises a solid amorphous dispersion, a disintegrant, and a porosigen, the disintegrant being selected from crospovidone, croscarmellose sodium, lower alkyl-substituted hydroxypropyl cellulose and mixtures thereof, and the porosigen being selected from microcrystalline cellulose, dibasic calcium phosphate (anhydrous and/or dihydrate) and mixtures thereof. The tablet is formed so that it has a strength of at least 5 Kp/cm$^2$ and a porosity of at least 0.15.

Other conventional formulation excipients may be employed in the dosage forms of the invention, including those excipients well known in the art, e.g., as described in *Remington's Pharmaceutical Sciences* (18th ed. 1990). Generally, excipients such as surfactants, pH modifiers, fillers, matrix materials, complexing agents, solubilizers, pigments, lubricants, glidants, flavorants, and so forth may be used for customary purposes and in typical amounts without adversely affecting the properties of the compositions.

One very useful class of excipients is surfactants, preferably present from 0 to 10 wt %. Suitable surfactants include fatty acid and alkyl sulfonates; commercial surfactants such as benzalkonium chloride (HYAMINE® 1622 from Lonza, Inc. of Fairlawn, N.J.); dioctyl sodium sulfosuccinate (DOCUSATE SODIUM from Mallinckrodt Specialty Chemicals of St. Louis, Mo.); polyoxyethylene sorbitan fatty acid esters (TWEEN® from ICI Americas Inc. of Wilmington, Del.; LIPOSORB® 0-20 from Lipochem Inc. of Patterson N.J.; CAPMUL® POE-0 from Abitec Corp. of Janesville, Wis.); natural surfactants such as sodium taurocholic acid, 1-palmitoyl-2-oleoyl-sn-glycero-3-phosphocholine, lecithin, and other phospholipids and mono- and diglycerides; and mixtures thereof. Such materials can advantageously be employed to increase the rate of dissolution by, for example, facilitating wetting, or otherwise increase the rate of drug release from the dosage form.

Inclusion of pH modifiers such as acids, bases, or buffers may also be beneficial in an amount of from 0 to 10 wt %. Acidic pH modifiers (e.g., acids such as citric acid or succinic acid) retard the dissolution of the pharmaceutical composition when the dispersion polymer is anionic. Alternatively, basic pH modifiers (e.g., sodium acetate or amines) enhance the rate of dissolution of the same types of pharmaceutical composition.

Examples of other matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof.

Examples of surface active agents include sodium lauryl sulfate and polysorbate 80.

Examples of drug-complexing agents or solubilizers include the polyethylene glycols, caffeine, xanthene, gentisic acid and cylodextrins.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc and zinc stearate.

Examples of glidants include silicon dioxide, talc and cornstarch.

The tablets may also be coated with a film coating using procedures well known in the art. These coatings may be used to mask taste, improve appearance, or facilitate swallowing of the dosage form. Such coatings may be fabricated by any conventional means including fluidized bed coating, spray-coating, pan-coating and powder-coating using aqueous or organic solvents.

The following is an exemplary method for forming immediate release tablets of the present invention, the tablets comprising solid dispersions of a low solubility drug and a concentration-enhancing polymer. In this method, about 10 to 80 wt % of the solid amorphous dispersion, about 5 to about 70 wt % of dibasic calcium phosphate anhydrous, about 5 to about 70 wt % of microcrystalline cellulose, and about 5 to about 25 wt % of crospovidone may first be blended in, for example, a V-blender, followed by de-lumping through a screen and then addition of about 0.2 to about 2 wt % of a lubricant such as magnesium stearate and further blending. The blend may then be densified using a roller compactor. The size of the compacts may then be reduced by milling to form granules with a mean granule size of about 100 μm to 400 μm. An additional portion of lubricant may then be added to the granules and the mixture blended prior to tableting. The blends are then compressed into tablets weighing from about 100 to about 1000 mg on a conventional tablet press such as a Kilian T-100.

Enteric-Coated Dosage Forms

In some cases, to avoid poor toleration or to avoid degradation of the drug in an acidic environment, it is desired that the solid amorphous dispersion not be released in the stomach. In these instances, the dosage form may also be overcoated with one or more pH-sensitive coating compositions, commonly referred to in the pharmaceutical arts as "enteric" coatings, by conventional procedures in order to delay the release of drug until it reaches the duodenum or small intestine. pH-sensitive polymers suitable as enteric coatings include those which are relatively insoluble and impermeable at the pH of the stomach, but which are more soluble or disintegrable or permeable at the pH of the duodenum and small intestine. Such pH-sensitive polymers include polyacrylamides, phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (HPCP), hydroxypropyl ethylcellulose phthalate (HPECP), hydroxypropyl methylcellulose phthalate (HPMCP), HPMCAS, methylcellulose phthalate (MCP), carboxymethylethyl cellulose (CMEC), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac and copolymers of vinyl acetate and crotonic acid.

A preferred group of pH-sensitive polymers includes CAP, PVAcP, HPMCP, HPMCAS, anionic acrylic copolymers of methacrylic acid and methylmethacrylate, and copolymers of acrylic acid and at least one acrylic acid ester.

To apply the pH-sensitive coating to the tablets, the pH-sensitive polymer may first be dissolved in a suitable solvent to form a coating solution. Useful solvents for this purpose include ketones, such as acetone; alcohols, such as methanol, ethanol, isopropyl alcohol, n-propyl alcohol, and the various isomers of butanol; chlorinated hydrocarbons, such as methylene chloride; water; and mixtures of these solvents. The polymer may also be suspended in the solvent. The coating solution may also comprise a latex of the pH-sensitive polymer suspended in an aqueous solution.

The coating solution may also contain one or more plasticizers, such as polyethylene glycols, triethyl citrate, propylene glycols, diethyl phthalate, dibutyl phthalate, castor oil, triacetin and others known in the art. The coating solution may also contain one or more emulsifiers, such as polysorbate-80. Coating is conducted in conventional fashion, typically by dipping, spray-coating, or pan-coating.

Other features and embodiments of the invention will become apparent from the following examples that are given for illustration of the invention rather than for limiting its intended scope.

Example 1

The following process was used to form a spray-dried dispersion containing 25 wt % of the poorly water-soluble drug 4-[(3,5-bis-trifluoromethyl-benzyl)-methoxycarbonylamino]-2-ethyl-6-trifluoromethyl-3,4-dihydro-2H-quinoline-1-carboxylic acid ethyl ester (Drug 1) and 75 wt % HPMCAS-HG (AQUOT-HG from Shin Etsu).

First, a feed solution was formed containing 2.5 wt % Drug 1 (250 g), 7.5 wt % HPMCAS-HG (750 g), and 90 wt % acetone (9000 g) as follows. The HPMCAS and acetone were combined in a container and mixed for 2 hours, causing the HPMCAS to dissolve. The resulting mixture had a slight haze after the entire amount of polymer had been added. Next, Drug 1 was added directly to this mixture, and the mixture stirred for an additional 2 hours. This mixture was then filtered by passing it through a filter with a screen size of 250 μm to remove any large insoluble material from the mixture, thus forming the feed solution.

The feed solution was pumped using a high pressure gear pump (Zenith Z-Drive 2000) to a Niro PSD-1 Portable Spray-Dryer equipped with a liquid feed process vessel and a pressure nozzle (Model SK 71-16 from Spraying Systems, Inc.). The dryer was also equipped with a 9-inch drying chamber extension to increase the length and volume of the drying chamber, which increased the residence time within the dryer, which allowed the product to dry before reaching the collection chamber of the dryer. The dryer was also equipped with a gas-dispersing means for introduction of the drying gas to the spray drying chamber. The gas-dispersing means consisted of a plate coextensive with the interior of the drying chamber (about 0.8 m diameter) and bearing a multiplicity of 1.7 mm perforations occupying about 1% of the surface area of the plate. The perforations were uniformly distributed across the plate, except that the density of perforations at the center 0.2 m of the diffuser plate was about 25% of the density of perforations in the outer part of the diffuser plate. The use of the diffuser plate resulted in organized plug flow of drying gas through the drying chamber and dramatically decreased product recirculation within the dryer. The nozzle was arranged flush with the gas-disperser plate during operation. The spray solution was pumped to the spray drier at about 195 g/min at a pressure of about 100 psig. Nitrogen drying gas was delivered to the gas-disperser plate at an inlet temperature of about 106° C. The evaporated solvent and wet drying gas exited the dryer at a temperature of 45±4° C. The spray-dried dispersion formed by this process was collected in a cyclone, and had a residual solvent content of 3.0 wt %, a bulk specific volume of about 5 cm³/g, and a mean particle diameter of about 80 μm.

The dispersion formed using the above procedure was subjected to secondary drying in a Gruenberg single-pass convection tray dryer operating at 40° C. for about 3 hours. Following drying, the dispersion was then equilibrated with ambient temperature and humidity.

Example 2

Immediate release tablets containing 30 mg and 120 mg of active Drug 1 were formed from the spray-dried dispersion of Example 1. The tablets contained 60 wt % of the dispersion of Example 1, 14.75 wt % microcrystalline cellulose (AVICEL PH105), 10 wt % crospovidone (POLYPLASDONE), 0.5 wt % magnesium stearate, and 14.75 wt % anhydrous dibasic calcium phosphate (EMCOMPRESS, Penwest Pharmaceuticals Co., Patterson, N.J.). The following procedure was used to form the tablets. The dispersion, the microcrystalline cellulose, and the crospovidone were mixed for 15 minutes in a twin shell blender. Half of the magnesium stearate was then added to the blender and mixed for an additional 5 minutes. The resulting blend had a specific volume of 4.2 to 5.0 cc/g.

This blend was then compressed into ribbons using a TF-mini compactor using smooth rollers, a rotation speed of 4 rpm, a roller back pressure of 25 to 30 kg/cm² and an auger speed of 25 to 30 rpm. The compressed material was de-dusted on a 12-mesh (1680 μm) screen, and then milled using a Fitzpatrick M5A mill fitted with a rasping bar and a 0.033-inch (20 mesh, 840 μm) Conidur rasping plate. Mill rotation was in the knife direction at 500 rpm. The mean particle size by screen analysis of the granulated material was 223 μm and the specific volume was 2.2 cc/g.

The granulated material was added to a twin shell blender and the anhydrous dibasic calcium phosphate was added and the mixture blended for 15 minutes. The final amount of magnesium stearate was added and the granulation blended an additional 5 minutes. The mean particle size of this final granulated material was 161-188 μm, and the specific volume was 1.8 to 2.0 cc/g.

A Kilian T-100 rotary tablet press was used to make tablets containing 30 mgA Drug 1 ("mgA" means the amount of active drug in milligrams), using 5/16" standard round concave (SRC) tooling. To form the tablets, 200 mg of the final granulated material was placed in the tablet press. A pre-compression force of approximately 2 kN was used and the compression force was set to deliver tablets having a hardness of 7 kiloponds (kP), as measured on a Schleuniger tablet hardness tester, Model 6D. The "strength" of a tablet was calculated by dividing the tablet's hardness by the maximum cross-sectional area of the tablet. For the 5/16-inch SRC tooling, the maximum cross-sectional area is 0.495 cm². Thus, the strength of the tablets was 7 kP÷0.495 cm², or 14.1 kP/cm².

Disintegration time of the tablets was measured according to the USP XXIV disintegration test procedure, using a Erweka ZT-71 disintegration tester, as follows. One tablet is placed in each of six tubes of the basket-rack assembly, and the tester is operated using deionized water as the disintegration medium maintained at a temperature of 37° C. Complete disintegration is defined as that state in which any residue of the tablet remaining on the screen of the test apparatus, except fragments of insoluble coating, is a soft mass having no palpable firm core. A disintegration time limit is established empirically, and is defined as the minimum time for at least 16 of 18 tablets to disintegrate completely. At the end of the time limit, the basket is lifted from the water, and the degree of disintegration of the tablets is observed. The mean disintegration time for the tablets was established to be less than 10 seconds.

A Kilian T-100 rotary tablet press was used to make tablets containing 120 mgA Drug 1, using oval (0.3437 inch×0.6875 inch) tooling having a maximum cross-sectional area of 1.197 cm². To form the tablets, 800 mg of the final granulated material was placed in the tablet press. A pre-compression force of approximately 2 kN was used and the compression force was set to deliver tablets having a hardness of 16 kP, resulting in a tablet strength of 13.4 kP/cm². The mean disintegration time for the tablets was established at less than 15 seconds.

Drug 1 dissolution from the tablets of Example 2 was measured using an in vitro test. First, a dissolution medium consisting of a simulated intestinal buffer solution was made by dissolving 6.8 g of $KH_2PO_4$ in 750 mL of deionized water with 85 mL 0.2M NaOH. Water was added for a final volume of 1 L. The pH was adjusted to 6.8±0.1 using 0.2M NaOH. Next, 0.5 wt % sodium lauryl sulfate was added to the buffer. A 900 mL sample of this solution was added to each of two vessels in a VanKel dissolution testing apparatus with automatic sampling. The solution temperature was maintained at 37° C., and stirred with a paddle speed of 100 rpm. This dissolution medium acted as a sink for the 120 mgA tablets. After equilibration to 37° C., a tablet of Example 2 was added to each vessel containing the buffer solution, resulting in a Drug 1 concentration of 130 μgA/mL, assuming all of the drug had dissolved. Samples were collected at 5, 15, 20, 35, 45, 60, 75, 90, 120 and 180 minutes, and then analyzed by HPLC using a Waters Symmetry $C_8$ column. The mobile phase consisted of 0.2 vol % $H_3PO_4$ (in water)/methanol in the ratio of 15/85 (vol/vol). Drug 1 concentration was calculated by comparing UV absorbance at 256 nm to the absorbance of Drug 1 standards. The results (average of two tests) are reported in Table 1.

TABLE 1

| Time (min) | Drug 1 Concentration (μgA/mL) | Drug 1 Released (wt %) |
|---|---|---|
| 0 | 0 | 0 |
| 5 | 49 | 37 |
| 15 | 114 | 87 |
| 20 | 123 | 94 |
| 35 | 126 | 96 |
| 45 | 126 | 96 |
| 60 | 125 | 95 |
| 75 | 128 | 98 |
| 90 | 127 | 97 |
| 120 | 127 | 97 |
| 180 | 131 | 100 |

These data show that the dosage form of Example 2 released 87 wt % of Drug 1 in 15 minutes.

Examples 3-6

These examples show that the amount of dispersion in immediate release tablets can be increased while maintaining satisfactory tablet properties. Tablets containing 50 wt %, 65 wt %, 70 wt %, and 75 wt % dispersion were made and tested for hardness and disintegration time.

For Example 3, immediate release tablets were made containing 50 wt % of the dispersion of Example 1, 12.0 wt % microcrystalline cellulose (AVICEL PH200), 12.5 wt % crospovidone, 0.5 wt % magnesium stearate, and 25.0 wt % anhydrous dibasic calcium phosphate. All ingredients except the magnesium stearate were mixed for 20 minutes in a Turbula blender. Half of the magnesium stearate was then added to the blender and mixed for an additional 5 minutes. The resulting mixture was formed into compacts using an F-Press, and the compacts were ground with a mortar and pestle until all the granules passed a 20-mesh screen. The second half of the magnesium stearate was added to the ground mixture and blended in the Turbula blender for 5 minutes. A Kilian T-100 rotary tablet press with ⅜-inch flat-beveled (FB) tooling having a 0.713 cm² cross-sectional area was used to make 250 mg tablets.

For Example 4, immediate release tablets were made as in Example 3 containing 65 wt % of the dispersion of Example 1, 10.0 wt % microcrystalline cellulose, 10.0 wt % crospovidone, 0.5 wt % magnesium stearate and 14.5 wt % anhydrous dibasic calcium phosphate.

For Example 5, immediate release tablets were made as in Example 3 containing 70 wt % of the dispersion of Example 1, 10.0 wt % microcrystalline cellulose, 10.0 wt % crospovidone, 0.5 wt % magnesium stearate and 9.5 wt % anhydrous dibasic calcium phosphate.

For Example 6, immediate release tablets were made as in Example 3 containing 75 wt % of the dispersion of Example 1, 7.5 wt % microcrystalline cellulose, 7.5 wt % crospovidone, 0.5 wt % magnesium stearate and 9.5 wt % anhydrous dibasic calcium phosphate.

The tablets of Examples 3-6 were formed using three different compression forces, measured by the Kilian tablet press. Tablets made at each compression force were tested for hardness on a Schleuniger tablet hardness tester, Model 6D. Disintegration times were measured as in Example 2. Results of compression, hardness, strength and disintegration measurements for the tablets of Examples 3-6 are reported in Table 2.

TABLE 2

| Example No. wt % Dispersion | Compression (kN) | Hardness (kP) | Strength (kP/cm²) | Mean Disintegration Time (sec) |
|---|---|---|---|---|
| 3 | 5.5 | 5.0 | 7.0 | 5 |
| 50 wt % | 13.5 | 10.9 | 15.3 | 9 |
|  | 20.8 | 13.9 | 19.5 | 11 |
| 4 | 6.5 | 7.4 | 10.4 | 5 |
| 65 wt % | 15.0 | 13.0 | 18.2 | 11 |
|  | 23.1 | 14.1 | 19.8 | 15 |
| 5 | 6.7 | 8.7 | 12.2 | — |
| 70 wt % | 16.5 | 13.5 | 18.9 | — |
|  | 22.1 | 14.5 | 20.3 | 16 |
| 6 | 6.5 | 8.5 | 11.9 | — |
| 75 wt % | 17.0 | 12.8 | 18.0 | — |
|  | 22.3 | 14.4 | 20.2 | 19 |

Examples 7-9

In Examples 7-9, the effects of various porosigens on tablet properties were examined. The dispersion of Example 1 was formulated with 20% extragranular microcrystalline cellulose (AVICEL PH102), 20% of a mixture of microcrystalline cellulose and colloidal silicon dioxide (PROSOLV 90), or 20% anhydrous dibasic calcium phosphate (EMCOMPRESS), all as dry granulated blends with no lubricant. Hardness, disintegration time, and porosity of the tablets were measured as noted above.

For Example 7, immediate release tablets were made containing 70 wt % of the dispersion of Example 1, 20.0 wt % microcrystalline cellulose and 10.0 wt % crospovidone disintegrant. To form the tablets, the dispersion of Example 1 and the crospovidone were mixed in the Turbula blender for 10 minutes. The mixture was then formed into compacts on the F-Press. The compacts were milled with a mortar and pestle. The microcrystalline cellulose was added to the granules and mixed for 10 minutes in the Turbula blender. The granulation was then divided into 250 mg samples and the samples were compressed with the Killian tablet press using ⅜-inch FB tooling.

For Example 8, immediate release tablets were made as in Example 7 containing 70 wt % of the dispersion of Example 1, 20.0 wt % of the Prosolv 90 and 10.0 wt % crospovidone.

For Example 9, immediate release tablets were made as in Example 7 containing 70 wt % of the dispersion of Example 1, 20.0 wt % anhydrous dibasic calcium phosphate and 10.0 wt % crospovidone.

The tablets of Examples 7-9 were formed using three different compression forces and tested as in Examples 3-6 for compression, hardness, strength, disintegration times and porosity, the results of which are reported in Table 3. Tablet porosity was calculated using the equation given above.

TABLE 3

| Example No. wt % Porosigen | Compression (kN) | Hardness (kP) | Strength (kP/cm²) | Mean Disintegration Time (sec) | Porosity |
|---|---|---|---|---|---|
| 7 | 7.4 | 8.4 | 11.8 | 5 | 0.25 |
| 20 wt % | 17.6 | 13.7 | 19.2 | 9 | 0.21 |
| AVICEL | 26.6 | 13.6 | 19.1 | 10 | 0.20 |
| 8 | 7.7 | 11.1 | 15.6 | 6 | 0.24 |
| 20 wt % | 17.5 | 15.9 | 22.3 | 11 | 0.20 |
| PROSOLV 90 | 26.9 | 16.6 | 23.3 | 12 | 0.20 |
| 9 | 6.2 | 5.8 | 8.1 | 7 | 0.28 |
| 20 wt % | 14.4 | 11.4 | 16.0 | 17 | 0.21 |
| EMCOMPRESS | 21.9 | 12.8 | 18.0 | 19 | 0.19 |

As is apparent from the values reported in Table 3, all of the tablets of Examples 7-9 disintegrated rapidly in the aqueous use environment. There is also seen a correlation between porosity and disintegration time, namely, the lower the porosity, the longer the disintegration time.

Examples 10-11

In Examples 10-11, the effect of disintegrants on tablet properties was examined. The dispersion of Example 1 was formulated with 10 wt % croscarmellose sodium (AcDiSol) or 10 wt % crospovidone (POLYPLASDONE) as dry granulated binary blends with no lubricant. Hardness and disintegration of the tablets were measured as in previous Examples.

For Example 10, immediate release tablets were made containing 90 wt % of the dispersion of Example 1 and 10 wt % AcDiSol. To form the tablets, the dispersion of Example 1 and the AcDiSol disintegrant were mixed in the Turbula blender for 10 minutes. The mixture was then formed into compacts on the F-Press. The compacts were milled with a mortar and pestle. The milled granules were mixed for 4 minutes in the Turbula blender. The granulation was then divided into 250 mg samples and the samples were compressed with the Kilian tablet press using ⅜-inch FB tooling.

For Example 11, immediate release tablets were made as in Example 10 containing 90 wt % of the dispersion of Example 1 and 10 wt % POLYPLASDONE.

The tablets of Examples 10-11 were formed using three different compression forces and tested as described above for Examples 3-6. The measured compression, hardness, strength and disintegration measurements are reported in Table 4.

TABLE 4

| Example No. wt % Disintegrant | Compression (kN) | Hardness (kP) | Strength (kP/cm²) | Mean Disintegration Time (sec) | Porosity |
|---|---|---|---|---|---|
| 10 | 4.5 | 4.0 | 5.6 | 45 | 0.30 |
| 10 wt % | 6.9 | 7.9 | 11.1 | 55 | 0.23 |
| AcDiSol | 17.7 | 13.1 | 18.4 | 74 | 0.19 |
| 11 | 4.4 | 3.9 | 5.5 | 18 | 0.32 |
| 10 wt % | 8.1 | 9.0 | 12.6 | 29 | 0.24 |
| POLYPLASDONE | 19.7 | 11.8 | 16.5 | 31 | 0.20 |

As is apparent from the values in Table 4, tablet compression/hardness profiles and porosities were similar for the two blends, while disintegration was faster for the tablets of Example 11.

Example 12

Example 12 shows results of experiments to measure the swelling force generated by the disintegrant. Tablets containing disintegrants that cause more rapid swelling have faster disintegration times at comparable disintegrant levels.

To measure the swelling force of various disintegrants, the Dynamic Mechanical Analyzer experimental apparatus 10 shown in FIG. 1 was used. Compacts containing equivalent concentrations of disintegrant material only were made on a Carver press with ¼-inch tooling, then placed into the sample holder 11 and 90-150 μm diameter glass beads 13 were used to surround and support the compact in the liquid reservoir 12, thereby facilitating the compact's rapid and uniform exposure to liquid. A constant force of approximately 5 N was applied to the sample by probe 14. Water was then added to the liquid reservoir and the change in displacement of the probe was measured as a function of time. The work or swelling energy attributable to disintegrant swelling, measured in J/g disintegrant, was calculated from the mathematical expression noted above.

Figure 2:
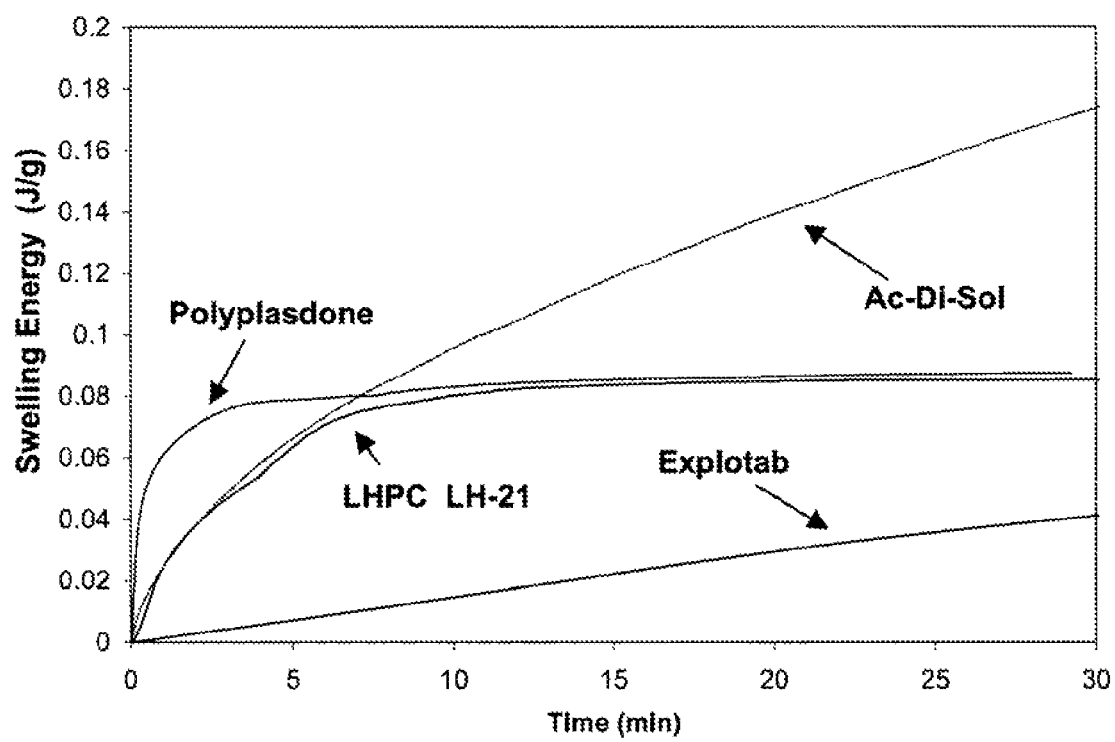
FIG. 2 presents the results of DMA tests for various excipients evaluated for use in the dosage forms of the present invention.

Four disintegrants—croscarmellose sodium (AcDiSol), lower alkyl-substituted hydroxypropyl cellulose (LHPC-LH21), crospovidone (POLYPLASDONE), and sodium starch glycolate (EXPLOTAB)—were tested using the method described above. Each of the four disintegrants had a unique and reproducible swelling energy curve as a function of time. The results are shown in FIG. 2. Tablet disintegration times, as a function of disintegrant type, followed the same trend as the rate of swelling—that is, the more rapidly the disintegrant caused swelling energy to develop, the faster the tablet disintegrated. These results quantitatively support the observation that tablets made with crospovidone (POLYPLASDONE) disintegrate more quickly than tablets made with croscarmellose sodium (AcDiSol) at equivalent disintegrant concentrations.

Example 13

A spray-dried dispersion was made containing 10 wt % of the poorly water-soluble drug 3-[(4-O-{4,6-bis(2-fluorophenylcarbamoyl)]-β-D-glucopyranolsyl-)β-D-flucopyranosyl]oxy-(3β,5α,25R)-spirostan-12-one (Drug 2) and 90 wt % HPMCAS-HG. First, a feed solution was formed containing 1.0 wt % Drug 2 (742 g), 9.0 wt % HPMCAS-HG (6519 g), 72 wt % acetone (52,150 g) and 18 wt % methanol (13,038 g). The feed solution was spray-dried with a Niro two-fluid external mix spray nozzle with nitrogen drying gas flow set at 2.6 bar and a feed rate of 192 g/min into the drying chamber of a Niro PSD-1 spray-dryer. The drying gas was maintained at a temperature of 140° C. at the inlet, while the drying gas and evaporated solvent exited the dryer at 51° C.

The resulting solid amorphous dispersion was collected via a cyclone and then dried further in a Gruenberg solvent tray dryer by spreading the dispersion onto polyethylene-lined trays to a depth of not more than 1 cm and then heating them at 40° C. for 16 hours. After such tray-drying, the solid dispersion contained 10 wt % Drug 2.

Examples 14-17

In Examples 14-17, the effect of disintegrants on tablet properties was examined for tablets containing a dispersion of Drug 2. For Example 14, immediate release tablets were made containing 65 wt % of the dispersion of Example 13, 19.0 wt % AVICEL PH102, 15 wt % AcDiSol and 1.0 wt % magnesium stearate. The dispersion, AVICEL and AcDiSol were mixed for 10 minutes in a Turbula blender. Half of the magnesium stearate was then added to the blender and mixed for an additional 4 minutes. The resulting mixture was formed into compacts using an F-Press, and the compacts were ground with a mortar and pestle until all the granules passed a 20-mesh screen. The second half of the magnesium stearate was then added to the ground mixture and blended in the Turbula blender for 4 minutes. The resulting granulation was then divided into 250 mg samples and the samples were compressed with the Kilian tablet press using ⁵⁄₁₆-inch FB tooling.

For Example 15, immediate release tablets were made as in Example 14 containing 65 wt % of the dispersion of Example 13, 19.0 wt % AVICEL PH102, 15 wt % POLYPLASDONE and 1.0 wt % magnesium stearate.

For Example 16, immediate release tablets were made as in Example 14 containing 65 wt % of the dispersion of Example 13, 19.0 wt % AVICEL PH102, 15 wt % EXPLOTAB and 1.0 wt % magnesium stearate.

For Example 17, immediate release tablets were made as in Example 14 containing 65 wt % of the dispersion of Example 13, 19.0 wt % Avicel PH102, 15 wt % LHPC-LH21 and 1.0 wt % magnesium stearate.

The tablets of Examples 14-17 were formed using four different compression forces and tested as in Examples 7-9 and the values for compression, hardness, strength, disintegration and porosity are reported in Table 5.

TABLE 5

| Example No. wt % Disintegrant | Compression (kN) | Hardness (kP) | Strength (kP/cm²) | Disintegration Time (sec) | Porosity |
|---|---|---|---|---|---|
| 14 | 2.7 | 7.6 | 15.4 | 60 | 0.30 |
| 15 wt % AcDiSol | 4.0 | 12.7 | 25.7 | 111 | 0.24 |
| | 8.4 | 19.5 | 39.4 | 246 | 0.17 |
| | 17.0 | 23.0 | 46.5 | 289 | 0.16 |
| 15 | 3.0 | 9.6 | 19.4 | 14 | 0.29 |
| 15 wt % POLYPLASDONE | 4.8 | 16.5 | 33.3 | 38 | 0.22 |
| | 10.5 | 22.5 | 45.5 | 171 | 0.17 |
| | 23.7 | 24.5 | 49.5 | 261 | 0.16 |

TABLE 5-continued

| Example No. wt % Disintegrant | Compression (kN) | Hardness (kP) | Strength (kP/cm²) | Disintegration Time (sec) | Porosity |
|---|---|---|---|---|---|
| 16 | 2.6 | 5.6 | 11.3 | 57 | 0.30 |
| 15 wt % | 4.2 | 10.1 | 20.4 | 117 | 0.23 |
| EXPLOTAB | 9.1 | 17.3 | 34.9 | 356 | 0.17 |
|  | 19.8 | 20.1 | 40.6 | 495 | 0.15 |
| 17 | 2.6 | 7.1 | 14.3 | 23 | 0.30 |
| 15 wt % | 4.3 | 12.5 | 25.3 | 50 | 0.23 |
| LHPC-LH21 | 8.5 | 18.4 | 37.2 | 240 | 0.17 |
|  | 20.5 | 20.3 | 41.0 | 345 | 0.15 |

The tablets made with POLYPLASDONE as the disintegrant (Example 15) achieved higher strength for a given compression force and faster disintegration times than the tablets of Examples 14, 16 or 17.

Control 1

For comparison to the tablets described in Examples 14-17, Control 1 tablets were formed using conventional immediate release dosage form tableting excipients. Tablets were made containing 62.5 wt % of the Drug 2 dispersion of Example 13, 20.0 wt % Fast Flow lactose (Foremost/Van Water and Rogers, Baraboo, Wis.), 13.5 wt % AVICEL PH102, 3.0 wt % AcDiSol, and 1.0 wt % magnesium stearate. The dispersion, lactose, AVICEL, AcDiSol, and half of the magnesium stearate were mixed for 10 minutes in a Turbula blender. The resulting mixture was formed into compacts using an F-Press, and the compacts were ground with a mortar and pestle until all the granules passed a 20-mesh screen. The second half of the magnesium stearate was added to the ground mixture and blended in the Turbula blender for 4 minutes. The granulation was then divided into 250 mg samples and the samples were compressed with the Kilian tablet press using 5/16-inch FB tooling.

The tablets of Control 1 were formed using three different compression forces and tested as described above for Examples 7-9. The compression, hardness, strength, and disintegration measurements for the tablets of Control 1 are reported in Table 6.

TABLE 6

| Compression (kN) | Hardness (kP) | Strength (kP/cm²) | Disintegration Time (sec) |
|---|---|---|---|
| 4.9 | 10.2 | 20.6 | 141 |
| 9.1 | 16.9 | 34.1 | 673 |
| 31.8 | 21.0 | 42.4 | 1236 |

As is apparent, Control 1 tablets made using conventional excipients showed much longer disintegration times for tablets of similar hardness compared to Examples 14-17. The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A high-loading immediate release dosage form comprising:
   an immediate release, disintegrable, compressed blend dosage form, comprising
   (a) at least 50 wt % of a solid amorphous dispersion, said dispersion comprising a low solubility drug and a concentration-enhancing polymer selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, and blends thereof, wherein the amount of drug in crystalline form in said dispersion does not exceed 10 wt %, said polymer being present in said dispersion in an amount of a drug-to-polymer weight ratio greater than 0.05 and less than 2.5,
   (b) at least 5 wt % of a disintegrant, and
   (c) a porosigen,
   wherein said immediate release dosage form has a porosity of at least 0.15, and disintegrates in 10 minutes or less following introduction to an in vitro disintegration medium of deionized water at 37° C.

2. The dosage form of claim 1 wherein said porosigen is present in an amount of at least 10 wt %.

3. The dosage form of claim 1 or 2 wherein said porosigen is selected from the group consisting of microcrystalline cellulose, dibasic calcium phosphate anhydrous, dibasic calcium phosphate dihydrate, tribasic calcium phosphate, monobasic sodium phosphate, dibasic sodium phosphate, calcium carbonate, calcium sulfate dihydrate, calcium sulfate, silicon dioxide, magnesium aluminum silicate, magnesium carbonate, and mixtures thereof.

4. The dosage form of claim 3 wherein said porosigen is selected from the group consisting of dibasic calcium phosphate anhydrous and dibasic calcium phosphate dihydrate.

5. The dosage form of claim 1 or 2 wherein said disintegrant is selected from the group consisting of crospovidone, croscarmellose sodium, lower alkyl-substituted hydroxypropyl cellulose, methyl cellulose, polacrilin potassium, sodium starch glycolate, and mixtures thereof.

6. The dosage form of claim 5 wherein said disintegrant is selected from the group consisting of crospovidone, croscarmellose sodium, and mixtures thereof.

7. The dosage form of claim 1 wherein said dosage form comprises 5 to 20 wt % of said disintegrant.

8. The dosage form of claim 7 wherein said disintegrant is crospovidone and said porosigen is dibasic calcium phosphate anhydrous.

9. The dosage form of claim 1 or 2 further comprising a coating.

10. The dosage form of claim 1 wherein the blend is a tablet having a strength of at least 5 Kp/cm², a porosity of at least 0.15, or both.

11. The dosage form of claim 1 consisting essentially of the immediate release, disintegrable, compressed blend dosage form, which consists essentially of the solid amorphous dispersion, the disintegrant, and the porosigen.

12. The high-loading immediate release dosage form of claim 1 wherein the compressed blend comprises granules with a mean granule size of about 100 μm to 400 μm.

13. A high-loading immediate release dosage form comprising:
   an immediate release, disintegrable, compressed blend dosage form, comprising
   (a) at least 50 wt % of a solid amorphous dispersion, said dispersion comprising a low solubility drug and a concentration-enhancing polymer selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, and blends thereof, wherein the amount of drug in crystalline form in said dispersion does not exceed 10 wt %, said polymer being present in said dispersion in an amount of a drug-to-polymer weight ratio greater than 0.05 and less than 2.5, (b) at least 5 wt % of a disintegrant, and (c) a porosigen; and (d) an enteric coating comprising a pH-sensitive polymer that is soluble or disintegrable at the pH of the duodenum and small intestine, wherein the compressed blend comprises granules with a mean granule size of about 100 μm to 400 μm, wherein said immediate release dosage form has a porosity of at least 0.15, and wherein the high-loading immediate release dosage form releases at least 70 wt % of the low solubility drug in 15 minutes following introduction to an in vitro dissolution medium comprising phosphate-buffered saline or model fasted duodenal solution at 37° C.

14. The high-loading immediate release dosage form of claim 1, wherein the immediate release dosage form has a porosity of at least 0.20.

15. The high-loading immediate release dosage form of claim 1, wherein the immediate release dosage form has a porosity of at least 0.25.

16. The high-loading immediate release dosage form of claim 1, wherein the immediate release dosage form releases at least 70 wt % of the low solubility drug within 15 minutes following introduction to the disintegration medium.

* * * * *